United States Patent [19]

Goble et al.

[11] Patent Number: 5,234,434
[45] Date of Patent: Aug. 10, 1993

[54] MUTLIPLE GUIDE SLEEVE DRILL GUIDE

[76] Inventors: E. Marlowe Goble, 850 E. 1200 North; W. Karl Somers, 651 N. 150 West, both of Logan, Utah 84321

[21] Appl. No.: 930,273

[22] Filed: Aug. 17, 1992

[51] Int. Cl.$^5$ .............................................. A61F 2/32
[52] U.S. Cl. ....................................... 606/96; 606/88; 606/98
[58] Field of Search ...................... 606/61, 62, 63, 64, 606/65, 96, 97, 98, 86-88

[56] References Cited

U.S. PATENT DOCUMENTS

| | | | |
|---|---|---|---|
| 4,235,428 | 11/1980 | Davis | 606/96 |
| 4,257,411 | 3/1981 | Cho . | |
| 4,535,768 | 8/1985 | Hourahane et al. . | |
| 4,541,424 | 9/1985 | Grosse | 606/98 |
| 4,668,233 | 5/1987 | Seedhom | 623/13 |
| 4,672,957 | 6/1987 | Hourahane . | |
| 4,708,139 | 11/1987 | Dunbar | 606/96 |
| 4,739,751 | 4/1988 | Sapega et al. . | |
| 4,823,780 | 4/1989 | Odensten et al. | 623/13 |
| 4,865,025 | 9/1989 | Buzzi | 606/96 |
| 4,901,711 | 2/1990 | Goble | 606/97 |
| 4,920,958 | 5/1990 | Walt et al. | 606/96 |
| 4,945,904 | 8/1990 | Bolton | 606/96 |
| 4,985,032 | 1/1991 | Goble | 606/96 |

FOREIGN PATENT DOCUMENTS 0126520 11/1984 European Pat. Off. .
2078528 1/1982 United Kingdom .

Primary Examiner—Michael A. Brown
Attorney, Agent, or Firm—M. Reid Russell

[57] ABSTRACT

The invention is in a double guide sleeve drill guide for use in an arthroscopic surgical procedure for replacement of a cruciate ligament in a straight ligament tunnel procedure that involves forming intersecting tunnels to the femoral and tibial sections of which straight ligament tunnel. The drill guide of the invention includes straight parallel reference and guide rods that are in the extend from a web member at right angles and are in the same plane, forming a U-shaped device, with the reference rod arranged for fitting into which straight ligament tunnel. The connection of which reference rod to the web member is adjustable along the web member for setting a spacing distance between which reference and guide rods, and equidistant markings are scribed along the reference rod as a scale. The guide rod mounts a pair of blocks, one fixed and one movable, with threaded holes formed through each for receiving a guide sleeve wherethrough a drill is turned, guiding drilling of holes that intersect which femoral and tibial tunnel sections. The fixed block is slightly movable to spread apart the threaded guide sleeve hole that is formed as two segments, to allow for passage of a drill sleeve slid therein. The two threaded guide sleeve hole sections are closed together to mesh with a guide sleeve threaded body portion, and a slot is formed in the guide rod that intersects the fixed block threaded guide sleeve hole to allow a drill or K-wire to pass therethrough.

9 Claims, 2 Drawing Sheets

MULTIPLE GUIDE SLEEVE DRILL GUIDE

BACKGROUND OF THE INVENTION

1. Field of the Invention

This invention relates to surgical devices and in particular to drill guides as are used in arthroscopic surgical procedures for knee reconstruction involving forming tibial and femoral tunnels that intersect the ligament points of origin in the knee joint, the invention for drilling holes through the distal femur and proximal tibia to intersect points along which tibial and femoral tunnels.

2. Prior Art

The invention, like a number of earlier drill guides of one or both of the inventors, is for use in an anterior or posterior cruciate ligament repair and/or replacement surgical procedure where tibial and femoral tunnel sections are formed in the distal femur and proximal tibia to pass through the ligament points of origin. With the knee bent appropriately, the tibial and femoral tunnel sections are straight and are for maintaining a ligament secured therein across the knee intra articular joint. The tunnels are referenced by the respective drill guides that are used for drilling intersecting holes from the distal femur and proximal tibia surfaces. Such intersecting holes are for passing a cross pin type mounting device to maintain a ligament end endosteally secured in a tunnel section. A drill guide of the inventors is shown in U.S. Pat. No. 4,901,711 and drill guides of one of the inventors are shown in U.S. Pat. No. 4,985,032, and U.S. patent applications in a "Sight Barrel Arthroscopic Instrument", Ser. No. 07/580,172, and in a "Femoral Tunnel Entry Drill Guide", Ser. No. 07/884,387. None of which earlier drill guides involves parallel reference and guide rods. Nor do such other devices provide for adjusting the spacing distance between the rods, by providing fixed and movable guide sleeve mounting blocks that are arranged with the guide rod. The blocks provide for setting a spacing distance between intersecting holes drilled from the knee surface into the straight ligament tunnel, in one drill guide setting.

The drill guides, as set out above, are for forming passages or holes that intersect points along ligament mounting tunnels. Unlike these devices and the present invention, a number of earlier drill guides have been used in knee arthroscopic surgical procedures for drilling, from without the knee, to a locator point within the knee intra articular joint. Examples of such earlier drill guides are shown in patents to Walt, et al, U.S. Pat. No. 4,920,958; to Sapega, et al, U.S. Pat. No. 4,739,751; to Cho, U.S. Pat. No. 4,257,411; to Hourahane, et al, U.S. Pat. No. 4,535,768; to Hourahane, U.S. Pat. No. 4,672,957; and a United Kingdom Patent to Lovell, et al, No. 2,078,528. Additionally, other earlier drilling devices have been developed for drilling tibial and femoral tunnel sections. None of which, however, have provided for drilling or forming intersecting holes or passages to the tunnel sections. Examples of such devices are shown in patents to Odensten, et al, U.S. Pat. No. 4,823,780; to Seedhom, et al, U.S. Pat. No. 4,668,233; and a European Patent to Seedhom, et al, No. 0,126,520. None of which devices provide a drill guide like that of the present invention for drilling, utilizing a single drill guide setting, a pair of holes to intersect, respectively, the femoral and tibial tunnel sections and for measuring the distance between the intersecting holes.

SUMMARY OF THE INVENTION

It is a principal object of the present invention in a multiple guide sleeve drill guide to provide a device with a reference rod for fitting into a straight tunnel that is formed in a patient's bent knee, the tunnel passing through the proximal tibia, extending across the intra articular joint and into the distal femur, and includes a guide rod that incorporates, respectively, a fixed femoral guide sleeve mounting block and an adjustable tibial guide sleeve mounting block that are for use in guiding drilling for forming intersecting holes into the femoral and tibial tunnel sections.

Another object of the present invention is to provide a U-shaped drill guide arranged to enable a surgeon to set a spacing distance between the external or guide rod and parallel reference rod by adjusting reference rod positioning along a web member, the reference rod is arranged for seating in the ligament tunnel.

Still another object or the present invention is to provide a drill guide where, with the reference rod seated in a straight ligament tunnel, a pair of intersecting holes can be drilled from without the knee to intersect, respectively, points along each of the femoral and tibial tunnel sections.

Still another object of the present invention is to provide a drill guide that includes an external or guide rod that mounts a pair of guide sleeve mounting blocks, each for receiving a guide sleeve turned therethrough, with a femoral guide sleeve mounting block maintained stationary and with a tibial guide sleeve mounting block arranged to be movable along the guide rod for adjusting the spacing distance between the guide sleeves.

Still another object of the present invention is to provide a drill guide that includes, as part of the fixed femoral guide sleeve mounting block, a quick release arrangement with a guide sleeve receiving hole formed therethrough for enabling the guide sleeve to be slid into or out of the sleeve receiving hole.

Still another object of the present invention is to provide a drill guide that includes an arrangement for setting the spacing distance between the fixed and movable guide sleeve mounting blocks, and for reading that distance off of a scale that is arranged along the reference rod, enabling a surgeon to select an optimum length of ligament for implanting in the straight ligament tunnel.

Still another object of the present invention is to provide a drill guide that is versatile, reliable and easy to use by a surgeon performing a cruciate ligament repair or replacement surgical procedure.

The multiple guide sleeve drill guide of the invention is for forming a pair of transverse holes to intersect, at right angles, respectively, spaced points along the femoral and tibial tunnel sections of a straight ligament tunnel and for determining the spacing distance between the intersecting holes. The drill guide consists of a U-shaped frame with parallel rods that are in the same plane and are connected at their ends to extend at right angles from a straight web member. The parallel rods are, respectively, a reference rod and an external or guide rod. The reference rod is for fitting into a prepared straight ligament tunnel formed in a patient's knee that passes through the proximal tibia, the knee intra articular joint at the ligament points of origin, and into the distal femur. The reference rod is positionable along the straight web member for setting the spacing distance between the parallel rods.

The external or guide rod supports a pair of guide sleeve mounting blocks that each having a threaded hole formed therethrough, each for receiving drill guide sleeves. The upper or femoral guide sleeve mounting blocks is stationary and includes a threaded drill sleeve mounting hole, a segment or section of which is an arcuate threaded portion that can be spread apart from that rest of the hole, opening the hole to allow a threaded body of the guide sleeve to slide therein. Whereafter, the movable arcuate threaded portion is moved back to where its threads a smooth or threaded surface on an opposing arcuate segment mounted opposite thereto from the threaded hole engage the threads of the guide rod threaded body. The upper or femoral block further includes a lateral slot formed from without the guide rod body for allowing passage of a drill or K-wire therethrough.

The second lower or movable tibial guide sleeve mounting block is movable longitudinally within the guide rod and includes a threaded drill sleeve receiving hole formed thereacross. To provide for movement of the tibial block for altering the threaded hole location along the external or guide rod, the movable block is arranged to slide within a cavity formed in which external or guide rod and includes a longitudinal threaded hole that is to receive a threaded body of a screw turned therethrough. The head end of the screw extends out from the external or guide rod end and is for manual turning for positioning the movable block along the guide rod.

A scale is scribed on the reference rod surface opposite to the guide sleeve fixed and movable mounting blocks threaded holes. The scale is for measuring the spacing distance between points of contact of a drill or K-wire fitted through guide sleeves fitted through which mounting blocks to intersect points along the reference rod scale, for selecting a length of natural or artificial ligament for fitting in the straight ligament tunnel.

THE DRAWINGS

These and other objects and features of the invention in a multiple guide sleeve drill guide will become more fully apparent from the following description in which the invention is described in detail in conjunction with the accompanying drawings:

FIG. 1 is a side elevation view of the multiple guide sleeve drill guide of the invention showing the outer surface of an external or guide rod with sections thereof broken away to expose fixed and movable guide sleeve mounting blocks;

FIG. 2 is a frontal view of the multiple guide sleeve drill guide of FIG. 1 showing, in broken lines, an arrangement of fixed and movable guide sleeve mounting blocks, as they are each fitted within the external or guide rods, the reference rod shown as including spaced transverse lines as a scale, with a straight web shown connected between the rods, with the reference rod shown exploded therefrom, the web member, as shown in broken lines, shown with spaced transverse holes formed therethrough for receiving a pin that is turned into the end of the reference rod;

Figures 3, 4, 5:
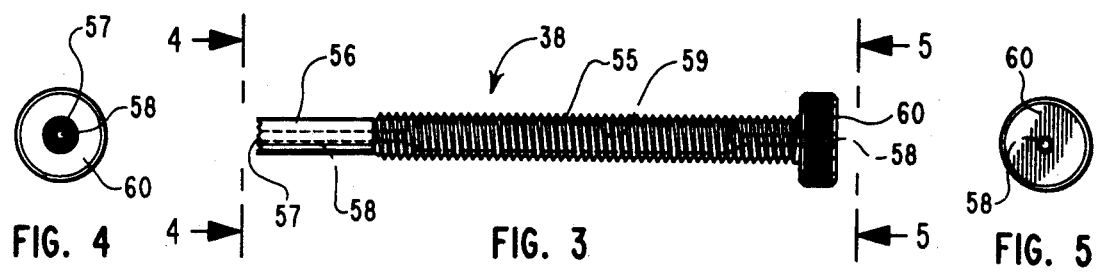
FIG. 3 is a side elevation view of a guide sleeve for turning in each of the mounting blocks threaded hole, and showing, in broken lines, a longitudinal passage formed therethrough.
FIG. 4 is an end sectional view of the guide sleeve taken along the line 4—4 of FIG. 3.
Figure 6:
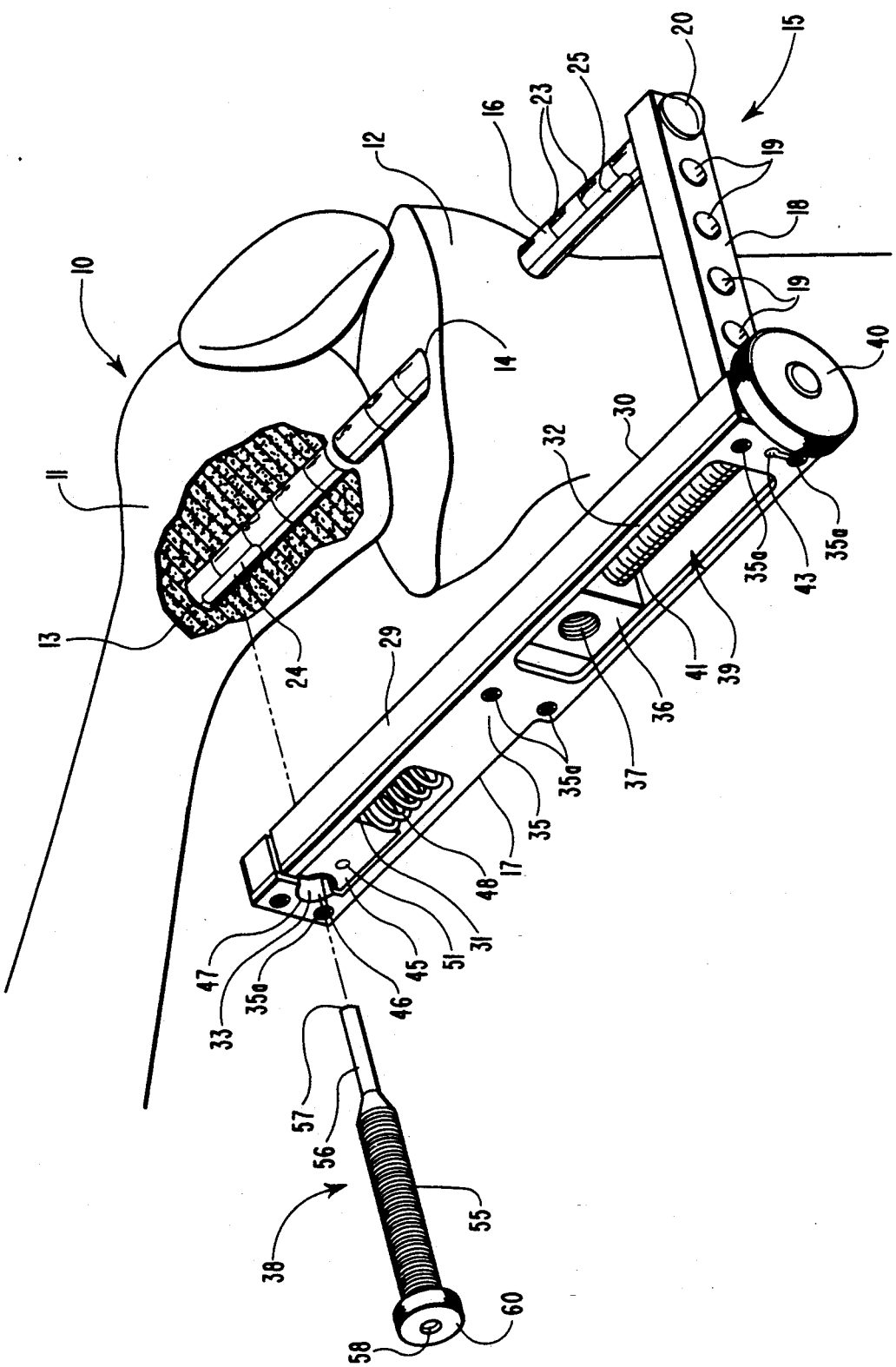

FIG. 5 is an opposite end sectional view of the guide sleeve taken along the line 5—5 of FIG. 3; and FIG. 6 is a profile perspective view of the multiple guide sleeve drill guide of the invention showing a section broken away from the outer surface of the external or guide rod, over the fixed block, and showing a patient's knee with the drill guide reference rod fitted into a straight anterior cruciate ligament tunnel, and showing the guide sleeve of FIG. 3 aligned for fitting in the threaded hole formed through the fixed block.

DETAILED DESCRIPTION

FIG. 6 shows a side elevation view of an intra articular knee joint 10, with the distal femur 11 and proximal tibia 12 shown bent to approximately a right angle. The knee 10 is shown as having had a straight ligament tunnel formed through the tibia anteromedial cortex, that passes through the ligament points of origin in the intra articular joint and into the femur endosteum, forming femoral and tibial tunnel sections 13 and 14, respectively, of the straight ligament tunnel. The straight ligament tunnel is for receiving a natural or prosthetic ligament fitted and secured therein. Into the straight ligament tunnel a reference rod 16 of a multiple guide sleeve drill guide 15 of the invention, hereinafter referred to as drill guide, is shown fitted.

Figures 1, 2:
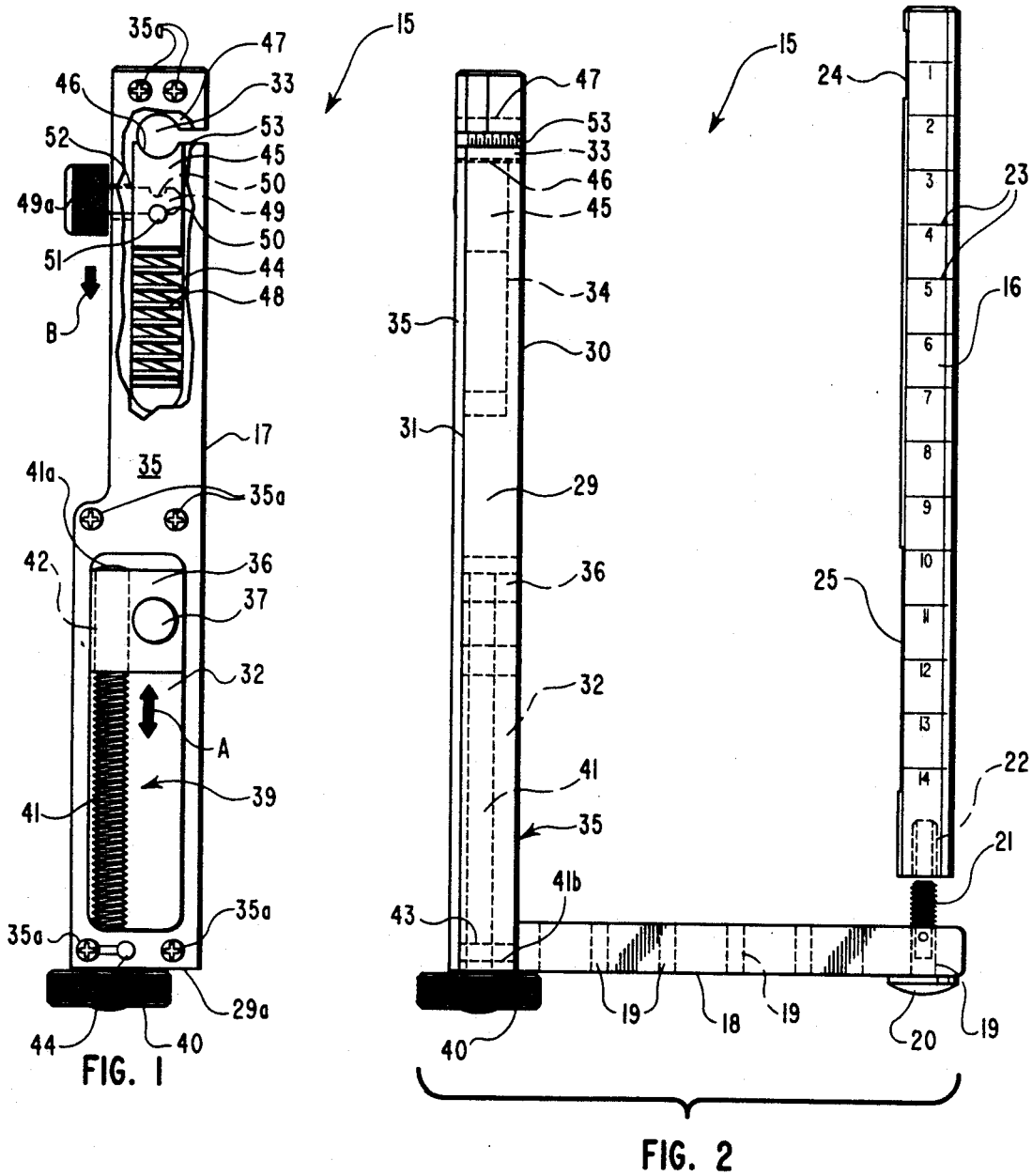

As shown in FIGS. 2 and 6, the drill guide 15 includes reference rod 16 and an external or guide rod 17, the ends of the rods are mounted to a straight web 18, the rods extend parallel and are in the same plane to one another. Shown in FIG. 6, with the reference rod 16 installed in the ligament tunnel, the guide rod 17 is positioned alongside the knee. A spacing distance between reference and guide rods 16 and 17 is set by the positioning of the reference rod along the straight web 18. Shown in FIG. 6, the web member 18 is formed of square rod stock, though, or course, other shapes of material could be utilized, and, as shown also in FIG. 2, the web member includes spaced transverse holes 19. The holes 19 are each for receiving a threaded shaft 21 of a broad head bolt 20 passed through one of the holes 19, the threaded shaft 21 for turning into threads of a tapped hole 22 that is axially formed into a lower end of the reference rod 16. The reference rod 16 is thereby positionable along the web member 18, providing for selecting an optimal spacing distance between the parallel reference and guide rods for a particular patient's knee.

The reference rod 16, as shown in FIGS. 2 and 6, includes transverse markings scribed thereon as scale 23, the markings are numbered from a transverse line identified as (1) that is proximate to the top end of the reference rod. The marking line (1), as set out below, is preferably aligned with a threaded hole formed through a fixed block 45 arranged in the guide rod 17. The scale markings continue along the reference rod to a transverse line identified as (14). In practice, a surgeon positions a movable block 36 of the guide rod 17 to where a threaded hole 37 formed through the movable block aligns with the reference rod scale markings 23, as set out below. The surgeon then turns a guide sleeve 38 through the threaded hole 37 and passes a drill, K-wire, or the like, through the guide sleeve 38 to intersect the reference rod along the scale. The point of intersection identifies a particular marking along the scale 23, providing a distance from the marking (1) for use in determining a required length of ligament, either natural or prosthetic, for installation in the straight ligament tunnel.

The reference rod 16, is preferably a round rod to conveniently fit into the prepared straight ligament tunnel, and includes flat surfaces 24 and 25 formed thereon. The flat surfaces are opposite, respectively, to the threaded holes 33 and 37 of the fixed and movable blocks 45 and 36 that are mounted to the guide rod 17. The flat surface 24 that is opposite to the fixed block 45 threaded hole 33 is accordingly short, with the flat surface 25 shown as long in comparison to accommodate the variable positioning of which movable block 36 along guide rod 17, as set out below.

The guide rod 17, as shown in FIGS. 1, 2 and 6, preferably incorporates a rectangular body 29, with the fixed and movable blocks 45 and 36 fitted therein, though other appropriate shape, such as square, could be utilized. As shown, the rectangle wide base surface 30 is opposite to the flat surfaces 24 and 25 of reference rod 16. The guide rod body 29 includes, for accommodating the movable block 36, a rectangular shaped opening 32 formed from the body 29 top surface 31 to the body 29 base surface 30, as shown best in broken lines in FIG. 2. The opening 32 is adjacent to the lower end 29a of the guide rod body. A hole is formed through the guide rod body end 29a that aligns with a longitudinally threaded hole 42 that is formed through the movable block 36, as shown in broken lines in FIG. 1, that is for receiving a threaded shaft 41 of an adjusting screw 39 turned therethrough, as set out below.

A cavity 34 for containing the fixed block 45 is formed in the guide rod body 29 that includes an arcuate smooth or threaded segment 47 formed in the cavity top end. The arcuate segment 47 is preferably smooth for facilitating travel of the guide sleeve 38 therethrough, the threads of an arcuate top surface 46 formed on the end of block 45 for mushing with a threaded body 55 of the guide sleeve, through the arcuate segment 47 could also include threaded segments turned therein for also mushing with the guide sleeve body, within the scope of this disclosure. The arcuate segment is a section of the threaded hole 33 that is formed through the fixed block, the threaded hole 33, whose function is set out below, and will approximately align with the scale marking (1) of the reference rod slot 24. Shown in broken lines in FIG. 2, the cavity 34 does not extend through the guide rod and is open too at the body 29 top surface 31. As shown in FIGS. 1 and 6, a cover plate 35 is mounted over the body 29 top surface 31, and is maintained thereto by screws 35a.

Shown in FIGS. 1 and 6, the fixed block 45 threaded hole 33 is formed through the guide rod body 29 and cover plate 35, with the rectangular opening 32 also formed through the guide rod body 29 and cover plate 35. Within the rectangular opening 32 the movable block 36 is maintained to slide up and down therein, as illustrated by double arrow A of FIG. 1. As shown, the movable block 36 includes the threaded hole 37 formed off-center across the rectangular movable block wide surfaces that is for receiving a guide sleeve 38, turned therein, as shown best in FIG. 3. For moving the movable block 36, the adjusting screw 39, that has a broad head 40 formed across an end thereof, is fitted and maintained through the body 29 lower end 29a. The adjusting screw has threaded shaft 41 that is turned through a threaded hole 42 off-set from the guide sleeve receiving hole 37 and formed longitudinally through the movable block 36. The threaded shaft 41 upper end 41a is arranged to extend beyond the edge of threaded hole 42, prohibiting the shaft from being turned out of the threaded hole. So arranged, a surgeon manually turning the adjusting screw 39 broad head 40 moves the movable block 36, as illustrated by arrow A. For maintaining the adjusting screw 39 in the body 29, prohibiting it from passage from the body end 29a, the threaded shaft 41 is necked inwardly into a notch 41b, shown in broken lines in FIG. 2, just above the broad head 40, and a smooth pin 43 is installed through the cover plate 35 and into the body 29 to pass alongside and through the notch 41b. The smooth pin 43 allows turning of the adjusting screw 39, that functions as a spindle, but blocks its turning out of the hole through body end 29a. So arranged, the movable block 36 can be moved, as illustrated by arrow A. Thereby, with a guide sleeve 38 turned through the movable block 36 threaded hole 37, a drill or K-wire, not shown, fitted through the guide sleeve and turned into the knee 10 will intersect a point along the reference rod 16 flat surface 25.

The fixed block 45 is a preferable rectangular section of material that has an arcuate top surface 46 wherein threads are formed to align with the threads or smooth surface of the arcuate segment 47 that is secured to or is integral to the body 29 top end. The fixed block arcuate top surface 46 and arcuate smooth or threaded segment 47, when closed together, form the threaded hole 33. For opening and closing which arcuate top surface 46 and arcuate smooth or threaded segment 47, the fixed block 45 is arranged to be slightly movable, as illustrated by arrow B in FIG. 1. To provide for closure, the fixed block 45 is biased upwardly by a spring 48 that is contained within cavity 44.

A shaft 49 is provided for moving the fixed block 45. The shaft 49 is fitted into a hole 52 formed through the side of the guide rod 17 body 29 and into fixed block 45, and arranged to be moved back and forth in hole 52. The shaft 49 includes a pair of top and bottom grooves 50 that interact with a set pin 51, as shown in FIG. 1. The set pin 51 is fitted across the fixed block 45, and shaft 49 is arranged to be manually moved back and forth in hole 52 by a surgeon depressing a broad head 49a end of the shaft that extends from the side of the guide rod body 29. Movement of the shaft 49 into the hole 52 causes the shaft groove 50 to ride up on the set pin 51, the set pin riding up the groove 50, to the adjacent shaft groove edge, displacing the fixed block 45 downwardly, as illustrated by arrow B. The fixed block 45 is opposed by spring 48, and spreads apart the fixed block arcuate top surface 46 from the arcuate smooth or threaded segment 47. The threaded hole 33 is thereby spread apart so as to allow a threaded body 55 of the guide sleeve 38 to be slid therein. When the guide sleeve 38 is appropriately positioned in threaded hole 33, and the inward force on shaft 49 releases spring 48 acting through the set pin 51 moves into the shaft groove 50. Thereby, the fixed block 45, under the urgings of the spring 48, is returned to the closed attitude shown in FIGS. 1 and 6, the threads of the threaded hole 33 meshing with the threads of the guide sleeve threaded body 55. The guide sleeve 38 can thereafter be turned into or out of the fixed block threaded hole 33 by turning a broad head 60 end thereof, as set out below.

As set out above, the guide sleeve 38 is easily removable from the threaded hole 33 by pushing shaft 49 head 49a towards the guide rod 17 body 29 side, moving the block arcuate top surface 46 away from the guide sleeve threads. Whereafter, the guide sleeve is conveniently pulled from the threaded hole 33, and off of a drill or K-wire, not shown. The drill or K-wire can then be slid through a slot 53 formed through the side of the guide rod body 29 into the threaded hole 33.

The guide sleeve 38, additional to the threaded body 55 includes, as shown in FIGS. 3 through 5, a smooth cylindrical section 56 that extends from an end of the threaded body that terminates in an end that has a radially serrated surface 57 formed thereacross. The serrations radiate out from a center hole 58 formed longitudinally through the guide sleeve. The center hole 58 is open in a central area 59 of the guide sleeve, as shown in broken lines in FIG. 3. The open center area 59 is for facilitating passing of a drill or K-wire , not shown, turned therethrough, allowing for bending of which turning drill or K-wire without binding. A broad head end 60 is secured across the end of the threaded body 55 for manual turning, with the center longitudinal hole 58 shown exiting the center of the broad head.

In practice, a surgeon after forming the femoral and tibial tunnel section 13 and 14 in the patients knee 10, with the knee bent so that the tunnel sections form a straight ligament tunnel, sets up the drill guide 15. The set up involves setting the spacing distance between the reference and guide rods 16 and 17, respectively. This is done by selecting a position for the reference rod 16 along the web member 18, and fitting the broad head bolt 20 through a transverse hole 19 thereat and turning the bolt threaded body 21 into a threaded hole 22 that is formed into the lower end of the reference rod 16. Further to the drill guide set-up, the spacing distance between the fixed and movable blocks 45 and 36, respectively, is set by manually turning the broad head 40 end of adjusting screw 41, that turns the adjusting screw threads into or out of the threaded longitudinal hole 42 of the movable block 36, moving the movable block as illustrated by double arrow A. By fitting a guide sleeve 38 through the respective threaded holes 33 and 37 of the fixed and movable blocks, and passing a drill or K-wire, not shown, through each guide sleeve, the points of contact with the flat sections 24 and 25 of the reference rod 16 are determined. The drill or K-wire end contact, as read from scale 23, provides a measure of the spacing distance between the intersecting holes as will be drilled. The spacing distance measure is used to select and proper length of a ligament, either natural or prosthetic, for implanting.

The surgeon then installs the drill guide reference rod 16 in the straight ligament tunnel, as shown in FIG. 6, to a distance therein where the scale marking (1) is at a point along the femoral tunnel section 13 where it is desired to drill an intersecting hole. With the shaft 49 displaced inwardly to move the set pin 51 of the fixed block 45 up the shaft groove 50 the fixed block arcuate top surface 46 is moved away from the arcuate threaded segment 47, allowing the guide sleeve 38 to be slid into threaded hole 33. The guide sleeve 38 is slid into threaded hole 33 to where the smooth shaft 56 radially serrated end 57 engages the patient's skin at their knee. Whereat, the shaft 49 head end 49a is released, the set pin 51 moving back into groove 50, under the urgings of the coil spring 48, to urge also moving the fixed block 45 arcuate top surface 46 upward to engage the threads of the threaded body 55 of the guide sleeve 38. The guide sleeve threads are also engaged by the arcuate threaded or smooth section 47 formed in the top end of cavity 34. Thereafter, turning the guide sleeve broad head 60 turns the threaded body 55 in the threaded hole 33, moving the guide sleeve appropriately toward or away from the patient's knee 10. A drill or K-wire, not shown, is then fitted through the guide sleeve bore 58 and turned into the femur to intersect the femoral tunnel section. Leaving this drill or K-wire in place, a second guide sleeve 38 is turned into the movable block 36 threaded hole 37 through an incision to where the guide sleeve serrated end 57 engages the tibia cortex. A drill or K-wire, not shown, is then fitted through the guide sleeve bore 58 and is turned into the tibia to intersect a select point along the tibial tunnel section 14.

If it is desired to release the drill guide 15 leaving the drills or K-wires in place, the shaft 49 then moved inwardly the set pin 51 displaced upwardly along shaft groove 50, displacing the arcuate top surface 46 out of engagement with the threads of the guide sleeve threaded body 55. The guide sleeve 38 can then be pulled out of the fixed block threaded hole 33 and off of the drill or K-wire, not shown, that remains in place. Thereafter, the guide rod 17 can be pivoted to move the drill or K-wire along slot 53 until it is free of the fixed block 45. Whereafter, a release of the reference rod 16 from the web member 18 can be provided by turning the broad head bolt 20 threaded shaft 21 out of the threaded hole 22 formed in the reference rod 16 end, releasing the web member 18 from the reference rod installed in the straight ligament tunnel. The guide sleeve 38 that is fitted through the movable rod threaded hole 37 can then be pulled off the tibial seated drill or K-wire, not shown, completing the drill guide 15 removal. The reference rod 16 can then be pulled from the straight ligament tunnel and replaced by a ligament fitted therein, under tension. Fasteners, such as set screw devices, can then be turned through which femoral and tibial tunnel sections intersecting holes, securing the ligament therein.

A preferred embodiment of the present invention in a double guide sleeve drill guide and its use has been shown and described herein. It should, however, be apparent that this disclosure is made by way of example only and that variations and modification to the apparatus and its use are possible within the scope of this disclosure without departing from the subject matter coming within the scope of the following claims and a reasonable equivalency thereof, which claims we regard as our invention.

We claim:

1. A double guide sleeve drill guide comprising, a straight reference rod for fitting into a prepared straight ligament tunnel, a straight web member, and means for securing a bottom end of said reference rod at a right angle to said web member; a straight guide rod that is secured at its bottom end to said web member, said reference and guide rods forming a right angle to said web member and are parallel to and in the same plane with one another, said guide rod further includes a fixed mounting block that has a guide sleeve receiving hole formed therethrough that is opposite to and aligns with a point on said reference rod, and a movable mounting block that has a guide sleeve receiving hole formed therethrough that is opposite to and aligns with said reference rod; means for moving said movable mounting block along said guide rod; and guide sleeves arranged for individual mounting in said fixed and movable mounting blocks guide sleeve holes for guiding a drilling means therethrough to intersect said reference rod.

2. A double guide sleeve drill guide as recited in claim 1, wherein the means for securing the reference rod end to the web member is a bolt type fastener having a threaded shaft for fitting through one of a number of holes formed at space interval along said, web member and fasten into a threaded hole formed longitudinally into said reference rod bottom end.

3. A double guide sleeve drill guide as recited in claim 1, further including a plurality of equally spaced markings that are numbered, in an ascending or descending order, as a scale scribed across the reference rod, one of said markings is aligned with the guide sleeve hole formed through the guide rod fixed mounting block, and said reference rod surfaces opposite to said fixed mounting block guide sleeve hole and the section of the reference rod to be aligned with the movable mounting block guide sleeve hole are flattened.

4. A double guide sleeve drill guide as recited in claim 1, wherein the guide rod is a rectangular section and the fixed mounting block is fitted in a cavity formed therein, proximate to a top end of said guide rod, and the guide sleeve hole formed in said fixed mounting block is threaded for receiving a threaded body portion of the guide sleeve turned therein.

5. A double guide sleeve drill guide as recited in claim 4, wherein the guide sleeve threaded hole is formed by a smooth arcuate segment that secured in a top end of the cavity that is opposed by a threaded arcuate top surface of the fixed block, said fixed block bottom surface is in contact with a spring means for biasing said fixed block threaded arcuate top, surface towards said smooth arcuate segment; said fixed mounting block further including a hole formed through the side of said guide rod body and into the side of said fixed block forming a right angle to the side of said guide rod body and is spaced apart from said threaded arcuate top surface, a straight cylindrical shaft means having a groove formed thereacross said hole formed through the guide rod body and the fixed mounting block is adapted to receive said cylindrical shaft means; a set pin that is secured through said fixed block and fits in said shaft means groove, said set pin, when said shaft means is displaced moves along said shaft means groove surface, displacing said fixed block against said spring biasing and spreading apart said arcuate threaded top surface and said smooth arcuate segment, with release of the displacing force on said shaft means, said set pin travels along and seats in said shaft means groove, closing said arcuate threaded top surface and said smooth arcuate segment together as the threaded hole; and means for displacing said shaft means.

6. A double guide sleeve drill guide as recited in claim 5, further including a slot formed into the guide rod body that intersects the threaded hole formed through the fixed block.

7. A double guide sleeve drill guide as recited in claim 4, wherein the movable block is a rectangular section of material that has the threaded guide sleeve hole formed off-center across the rectangular movable block wide surfaces, and said rectangular movable block is also drilled longitudinally, off-set from said guide sleeve receiving hole, from end to end, and said longitudinal hole is threaded to receive a threaded shaft fitted through a bottom end of the guide rod and is turned through said movable block longitudinal threaded hole arranged in the guide rod cavity, said movable block to travel up and down along said threaded shaft as it is turned; means for maintaining said threaded shaft to turn freely in said guide rod cavity; and means for turning said threaded shaft.

8. A double guide sleeve drill guide as recited in claim 1, wherein the guide sleeve consists of a cylindrical threaded body portion with a broad head on one end and with a smooth cylindrical shaft extending from the cylindrical threaded body portion other end, the end face of said smooth cylindrical shaft is radially serrated; and said guide sleeve includes a longitudinal hole formed therethrough.

9. A double guide sleeve drill guide as recited in claim 8, wherein the longitudinal hole formed through the guide sleeve is tapered outwardly, proximate to the broad head end, and tapers inwardly to the original hole diameter proximate to the junction of the cylindrical threaded body portion with the smooth cylindrical shaft.

* * * * *